United States Patent
Heinonen et al.

(10) Patent No.: US 8,992,672 B2
(45) Date of Patent: Mar. 31, 2015

(54) HOUSING AND HOUSING ASSEMBLY FOR SUBSTANCE REMOVING AN UNDESIRED RESPIRATORY GAS COMPONENT OF A RESPIRATORY GAS FLOW AND AN ARRANGEMENT FOR VENTILATING LUNGS OF A SUBJECT

(75) Inventors: Erkki Heinonen, Helsinki (FI); Janne Ranta, Espoo (FI); Mikael Alanen, Espoo (FI)

(73) Assignee: Carefusion Corporation, San Diego, CA (US)

( * ) Notice: Subject to any disclaimer, the term of this patent is extended or adjusted under 35 U.S.C. 154(b) by 665 days.

(21) Appl. No.: 13/169,405

(22) Filed: Jun. 27, 2011

(65) Prior Publication Data
US 2012/0325220 A1    Dec. 27, 2012

(51) Int. Cl.
| | | |
|---|---|---|
| *B01D 53/02* | (2006.01) | |
| *A61M 16/01* | (2006.01) | |
| *A61M 16/22* | (2006.01) | |
| *A61M 16/08* | (2006.01) | |

(52) U.S. Cl.
CPC .............. *A61M 16/01* (2013.01); *A61M 16/22* (2013.01); *A61M 16/0891* (2014.02)
USPC .................... 96/121; 128/204.18; 128/205.28

(58) Field of Classification Search
CPC . A61M 16/0045; A61M 16/10; A61M 16/22; A61M 19/00
See application file for complete search history.

(56) References Cited

U.S. PATENT DOCUMENTS

| | | | |
|---|---|---|---|
| 4,086,923 A | 5/1978 | Henkin | |
| 4,232,667 A | 11/1980 | Chalon et al. | |
| 6,619,289 B1 | 9/2003 | Mashak | |
| 7,533,669 B2 * | 5/2009 | Fuhrman et al. | 128/203.25 |
| 2005/0188990 A1 * | 9/2005 | Fukunaga et al. | 128/204.18 |
| 2007/0163588 A1 * | 7/2007 | Hebrank et al. | 128/204.18 |
| 2009/0266357 A1 * | 10/2009 | Varis et al. | 128/202.27 |
| 2009/0288659 A1 * | 11/2009 | Haveri et al. | 128/203.14 |
| 2010/0199993 A1 | 8/2010 | Koulechov et al. | |

FOREIGN PATENT DOCUMENTS

| | | |
|---|---|---|
| EP | 0611175 A1 | 8/1994 |
| GB | 1393909 A | 5/1975 |
| GB | 1558226 A | 12/1979 |
| WO | 9710020 A1 | 3/1997 |

OTHER PUBLICATIONS

Search Report from corresponding GB Application No. GB1211090.4 dated Oct. 19, 2012.

* cited by examiner

*Primary Examiner* — Christopher P Jones
(74) *Attorney, Agent, or Firm* — McDermott Will & Emery LLP

(57) ABSTRACT

A housing for a substance removing an undesired component of a respiratory gas is disclosed herein. The housing includes a first space for the substance and a first wall surrounding part of the first space. The housing also includes a first end, surrounding part of the first space, comprising a first opening for the gas communication with the first space, and a second end, surrounding part of the first space, comprising a second opening for the gas communication with the first space. The housing further includes a first channel between the first and the second end for the gas flow, the first channel comprising a first orifice at the first end and a second orifice at the second end. The first orifice, the first opening, the second orifice and the second opening are in flow communication with outside the housing.

20 Claims, 4 Drawing Sheets

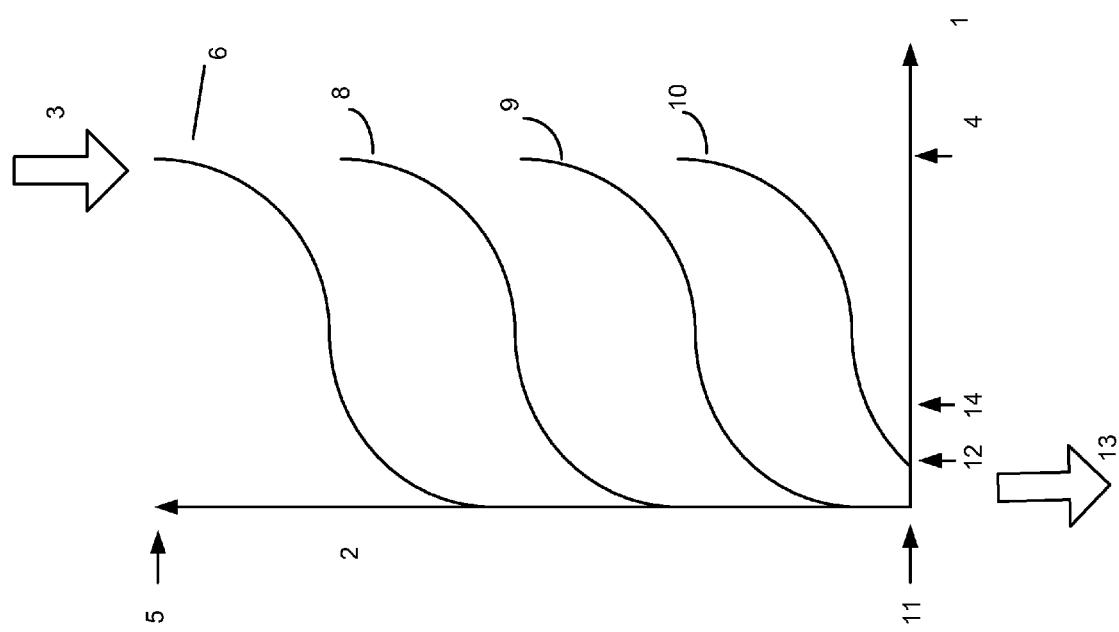

HOUSING AND HOUSING ASSEMBLY FOR SUBSTANCE REMOVING AN UNDESIRED RESPIRATORY GAS COMPONENT OF A RESPIRATORY GAS FLOW AND AN ARRANGEMENT FOR VENTILATING LUNGS OF A SUBJECT

BACKGROUND OF THE INVENTION

This disclosure relates generally to a housing and housing system for a substance removing an undesired respiratory gas component of a respiratory gas flow. The housing comprises a first space for receiving the substance, a first wall surrounding part of the first space, a first end operationally connected to the first wall and surrounding part of the first space, the first end comprising a first opening for the gas communication with the first space and a second end opposite the first end operationally connected to the first wall and surrounding part of the first space, the second end comprising a second opening for the gas communication with the first space. The housing also comprises a first channel between the first end and the second end for guiding the gas flow. This disclosure relates also to an arrangement for ventilating lungs of a subject.

Anesthesia machines are optimized for delivering anesthesia to a patient using volatile anesthetic agent liquids. In such systems, the anesthetic agent is vaporized and mixed into the breathing gas stream in a controlled manner to provide a gas mixture for anesthetizing the patient for a surgical operation. The most common volatile anesthetic agents are halogenated hydrocarbon chains, such as halothane, enflurane, isoflurane, sevoflurane and desflurane. Additionally, nitrous oxide (N2O) can be counted in this group of volatile anesthetic agents, although the high vapor pressure of nitrous oxide causes nitrous oxide to vaporize spontaneously in the high pressure gas cylinder, wherefrom it can be directly mixed as gas with oxygen. The anesthetizing potency of nitrous oxide alone is seldom enough to anesthetize a patient and therefore another volatile agent is used to support that.

Since the volatile anesthetic agents are expensive, they are effective greenhouse gases and further harmful to the atmospheric ozone layer, anesthesia machines have been developed to minimize the consumption of the gases. To keep patients anesthetized, a defined brain partial pressure for the anesthetic agent is required. This partial pressure is maintained by keeping the anesthetic agent partial pressure in the lungs adequate. During a steady state, the lung and body partial pressures are equal, and no net exchange of the anesthetic agent occurs between the blood and the lungs. However, to provide oxygen and eliminate carbon dioxide, continuous lung ventilation is required.

Anesthesia machines are designed to provide oxygen to the patient and eliminate carbon dioxide (CO2), while preserving the anesthetic gases. To meet these goals a re-breathing circuit is used. In this patient exhaled gas is reintroduced for inhalation. Before re-inhalation carbon dioxide must be removed from the gas, which is done with a carbon dioxide absorber. Before inhalation, the gas is supplied with additional oxygen and anesthetic agents based upon the patient demand. In this arrangement, the additional gas flow added to the re-breathing circuit can be less than 0.5 L/min although the patient ventilation may be 5-10 L/min. Such ventilation of the lung is carried out using a ventilator pushing inhalation gas with overpressure to patient lungs and then allowing that to flow out passively from the pressurized lungs to the breathing circuit.

Ventilation carries the breathing circuit oxygen to lungs for uptake to be burned in body metabolism. The outcome of this is CO2 that blood circulation transports to lungs wherefrom it becomes carried out with exhalation gas. Before re-inhalation the gas is guided through absorber for CO2 removal. Effective CO2 removal requires close contact with the breathing gas and the removing substance. To provide large contact area, the removing substance is therefore a surface of porous structure of granules that fill the cartridge. The form of this granular structure is guided by the flow resistance, the limitation of which is one key design goals of the breathing circuit. In absorber optimized for minimal resistance the gas flow path through the stacked granules is short and the flow distributes to wide area. In such structure the gas flows slowly because of large surface area providing time for reaction between the gas and absorbent granules.

The absorbers tend to have empty space above the granules. If the gas inlet and outlet to the absorber would be aligned to allow horizontal flow penetration through the cartridge, the flow would favor this empty space and the CO2 would leak through without getting absorbed. Therefore the gas flow must always penetrate through the absorbent on vertical direction.

CO2 absorption takes place in reaction with the absorber. This reaction begins once the CO2 enriched gas flow meets responsive absorbent. Using fresh absorber this occurs on the gas inlet to the absorber. FIG. 1 presents CO2 concentration on the abscissa 1 and absorber height on the ordinate 2. CO2 enriched gas 3 of concentration 4 gets in to the absorber at the top height 5 of the absorbent. When penetrating a distance within the absorbent the concentration reduces as indicated with the graph 6 to zero. Because of the granular structure of the absorbent, this absorption more exactly begins from the layer next to the gas inlet. This vertical height of graph 6 is called transfer zone. The gas CO2 concentration at the beginning of the transfer zone is the inlet concentration and at the end that is zero. Between the transfer zone the concentration declines gradually from inlet concentration to zero. Once the CO2 absorption occurs, the reactive absorbent wears out. As a result of this, the absorption does not occur any more at the inlet, which pushes the transfer zone forward along the gas flow path within the absorber as indicated successive graphs 8, 9, 10.

When the leading edge of the transfer zone reach the other end of the absorber bed 11, with increasing portion the gas flow penetrates through the absorber without the CO2 getting absorbed increasing the CO2 concentration 12 of the gas flowing out from the absorber 13. When the CO2 concentration of the passed gas reach maximum allowed concentration 14, the absorber must be changed. Typically this limit varies between 0.5% to 1%. At this point the absorber has however a lot of remaining absorption capacity left in the transfer zone.

To consume the whole absorption capacity, two absorbers, the first interfacing the breathing circuit and the second interfacing the first absorber, can be connected in series as illustrated on FIG. 2. In these circumstances, when the transfer zone reach the end 15 of the absorber 16, which is uppermost, another fresh absorber 16, which is lower one, in series absorbs the CO2 leaking through when the transfer zone penetrates there. Finally, when the transfer zone reaches the end 15 of the absorber, the absorption capacity of the uppermost absorber 16 has been totally utilized. At this moment the uppermost absorber is discharged, the lower absorber still having remainder capacity is moved to the place of the uppermost absorber, and a new absorber is assigned as the lower absorber.

The use of two absorbers connected in series is well known in anesthesia. This has however been replaced by single absorber cartridges because they allow compact breathing system in having gas inlet port 17 and gas outlet port 18 at one end of the absorber compared to the through-flow of the dual absorber solution where the ports are on opposite ends. This through-flow requires return flow path 19 within the breathing system to re-circulate the CO2 free gases for patient breathing. These channels, as part of the breathing circuit, require regular cleaning, which adds complexity to the anesthesia system maintenance.

BRIEF DESCRIPTION OF THE INVENTION

The above-mentioned shortcomings, disadvantages and problems are addressed herein which will be understood by reading and understanding the following specification.

In an embodiment, a housing for a substance removing an undesired respiratory gas component of a respiratory gas flow includes a first space for receiving the substance and a first wall surrounding part of the first space. The housing for a substance removing an undesired respiratory gas component of a respiratory gas flow also includes a first end operationally connected to the first wall and surrounding part of the first space, the first end comprising a first opening for the gas communication with the first space, and a second end operationally connected to the first wall and surrounding part of the first space, the second end comprising a second opening for the gas communication with the first space. The housing for a substance removing an undesired respiratory gas component of a respiratory gas flow further includes a first channel between the first end and the second end for guiding the gas flow, the first channel comprising a first orifice at the first end and a second orifice at the second end, the first orifice and the second orifice being in gas communication with the first channel. The first orifice and the first opening at the first end and the second orifice and the second opening at the second end of the housing are in flow communication with outside the housing.

In another embodiment, a housing assembly for a substance removing an undesired respiratory gas component of a respiratory gas flow includes a first housing having a first space for receiving the substance and a first wall surrounding part of the first space. The first housing also having a first end operationally connected to the first wall and surrounding part of the first space, the first end comprising a first opening for the gas communication with the first space and a second end operationally connected to the first wall and surrounding part of the first space, the second end comprising a second opening for the gas communication with the first space. The first housing further having a first channel between the first end and the second end for guiding the gas flow, the first channel comprising a first orifice at the first end and a second orifice at the second end, the first orifice and the second orifice being in flow communication with the first channel. The housing assembly for a substance removing an undesired respiratory gas component of a respiratory gas flow also includes a second housing having a second space for receiving the substance and a second wall surrounding part of the second space. The second housing also having a third end operationally connected to the second wall and surrounding part of the second space, the third end comprising a third opening for the gas communication with the second space and a fourth end operationally connected to the second wall and surrounding part of the second space, the fourth end comprising a fourth opening for the gas communication with the second space. The second housing further having a second channel between the third end and the fourth end for guiding the gas flow, the second channel comprising a third orifice at the third end and a fourth orifice at the fourth end, the third orifice and the fourth orifice being in flow communication with the second channel. The second opening of the first housing is adapted to be in flow communication with the third opening of the second housing to guide the gas flow between the first space and the second space and the second orifice of the first housing is adapted to be in flow communication with the third orifice of the second housing to guide the gas flow between the first orifice and the fourth orifice.

In yet another embodiment, an arrangement for ventilating lungs of a subject includes a ventilator for supplying a breathing gas for an inspiration and for receiving a breathing gas for an expiration, and a gas mixer for supplying a fresh gas for the subject breathing. The arrangement for ventilating lungs of a subject also includes a breathing circuit for connecting lungs of the subject, the ventilator and the gas mixer, the breathing circuit comprising an inspiration limb providing an inspiration gas including the fresh gas for the subject breathing, an expiration limb to discharge an expiration gas, and a housing assembly for a substance removing an undesired respiratory gas component of a respiratory gas flow. The housing assembly includes a first housing having a first space for receiving the substance and a first wall surrounding part of the first space. The first housing also having a first end operationally connected to the first wall and surrounding part of the first space, the first end comprising a first opening for the gas communication with the first space and a second end opposite the first end operationally connected to the first wall and surrounding part of the first space, the second end comprising a second opening for the gas communication with the first space. The first housing further having a first channel between the first end and the second end for guiding the gas flow, the first channel comprising a first orifice at the first end and a second orifice at the second end, the first orifice and the second orifice being in flow communication with the first channel. The housing assembly also includes a second housing having a second space for receiving the substance and a second wall surrounding part of the second space. The second housing also having a third end operationally connected to the second wall and surrounding part of the second space, the third end comprising a third opening for the gas communication with the second space and a fourth end opposite the third end operationally connected to the second wall and surrounding part of the second space, the fourth end comprising a fourth opening for the gas communication with the second space. The second housing further having a second channel between the third end and the fourth end for guiding the gas flow, the second channel comprising a third orifice at the third end and a fourth orifice at the fourth end, the third orifice and the fourth orifice being in flow communication with the second channel. The second opening of the first housing is adapted to be in flow communication with the third opening of the second housing to guide the gas flow between the first space and the second space and the second orifice of the first housing is adapted to be in flow communication with the third orifice of the second housing to guide the gas flow between the first orifice and the fourth orifice.

Various other features, objects, and advantages of the invention will be made apparent to those skilled in art from the accompanying drawings and detailed description thereof.

BRIEF DESCRIPTION OF THE DRAWINGS

FIG. 1 presents the progress of absorption transfer zone within an absorber;

DETAILED DESCRIPTION OF THE INVENTION

Specific embodiments are explained in the following detailed description making a reference to accompanying drawings. These detailed embodiments can naturally be modified and should not limit the scope of the invention as set forth in the claims.

Figure 3:
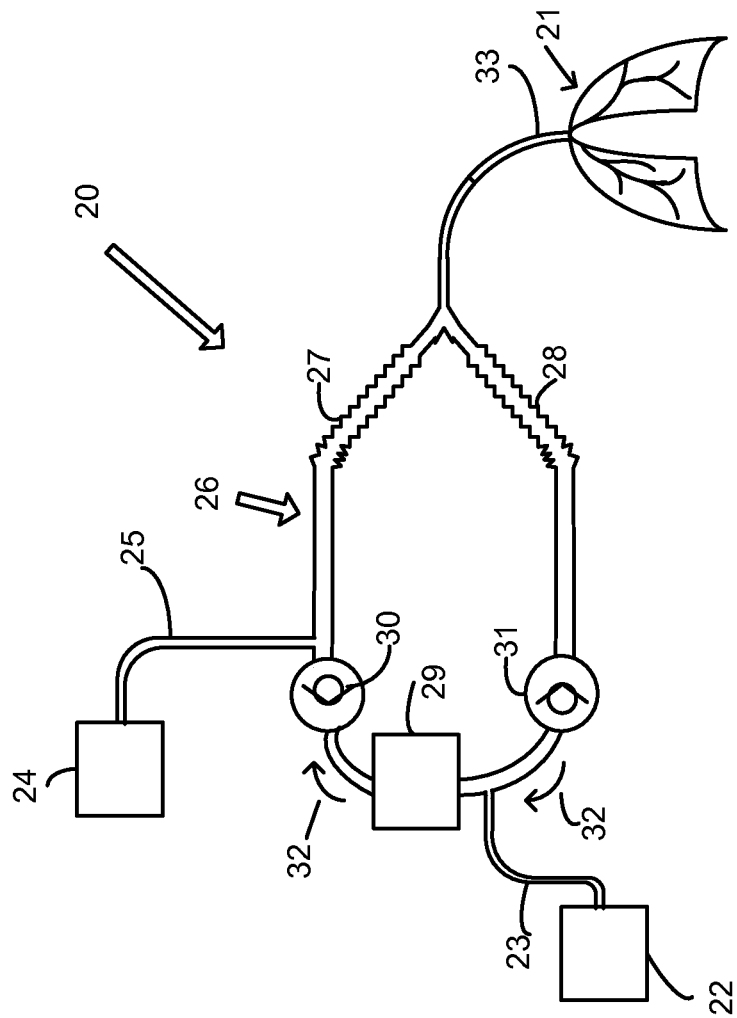
FIG. 3 illustrates an operational diagram of an arrangement for ventilating lungs of a subject.

In FIG. 3 an arrangement 20 for ventilating lungs 21 of a subject is disclosed. The arrangement comprises a ventilator 22 supplying in this specific embodiment along a tube 23 breathing gas to the lungs for an inspiration and receiving breathing gas for an expiration. The ventilator may be whichever well-known type e.g. drive gas based pneumatic flow-valve or mechanical piston driven. Also the arrangement comprises a gas mixer 24 supplying a fresh gas in this specific embodiment along a fresh gas tube 25 for the subject breathing, a breathing circuit 26 connecting lungs of the subject, the ventilator 22 and the gas mixer 24. The gas mixer may comprise an anesthetic agent supply (not shown in the figure) such as an anesthetic agent vaporizer providing anesthetic agent for the subject breathing.

The breathing circuit 26, which may be a re-breathing circuit, comprises an inspiration limb 27 providing an inspiration gas including the fresh gas for the subject breathing and an expiration limb 28 discharging an expiration gas. The ventilator is controlling the breathing circuit pressure through the tube 23. Also the breathing circuit comprises a housing assembly 29 for substance, which may be solid fluidal material, such as granules for removing an undesired respiratory gas component of a respiratory gas flow. Typical substance used in anesthesia is a carbon dioxide absorbing material, which may be soda-lime, a mixture of calcium hydroxide, sodium hydroxide, potassium hydroxide and water or any other substance that can extract CO2 from gas mixture e.g. molecular sieve or amines. The material may chemically react with carbon dioxide or otherwise remove it from the breathing gas. The housing assembly 29 may be detachable from the breathing circuit.

Typically the breathing circuit 26 also comprises directional valves 30 and 31 guiding the gas flow in the circuit on direction indicated by arrows 32. For inhalation the ventilator 22 increases the breathing circuit pressure by adding the gas flow from tube 23. Directional valves 30 and 31 guide the gas flow through the housing assembly 29, including the substance removing in this embodiment carbon dioxide from the breathing gas, to the inspiration limb 27 and further along a subject limb 33 to the subject's lungs 21. For expiration the ventilator 22 releases gases from the breathing circuit through the tube 23. For this purpose the ventilator 22 may e.g. operate an expiration valve (not shown in Figure). This will allow the gas flow from distended subject's lungs through the subject limb 33 to the expiration limb 28 and further through the directional valve 31 to the tube 23. The directional valve 23 prevents the gas flow from the subject's lungs to enter the inspiration limb 27 hereby maintaining the inspiration limb free from CO2. Instead, the exhaled gas is rich of CO2 that needs to be removed before being re-circulated for the inspiration, which is done in the housing assembly 29 including the substance removing carbon dioxide.

Figure 4:
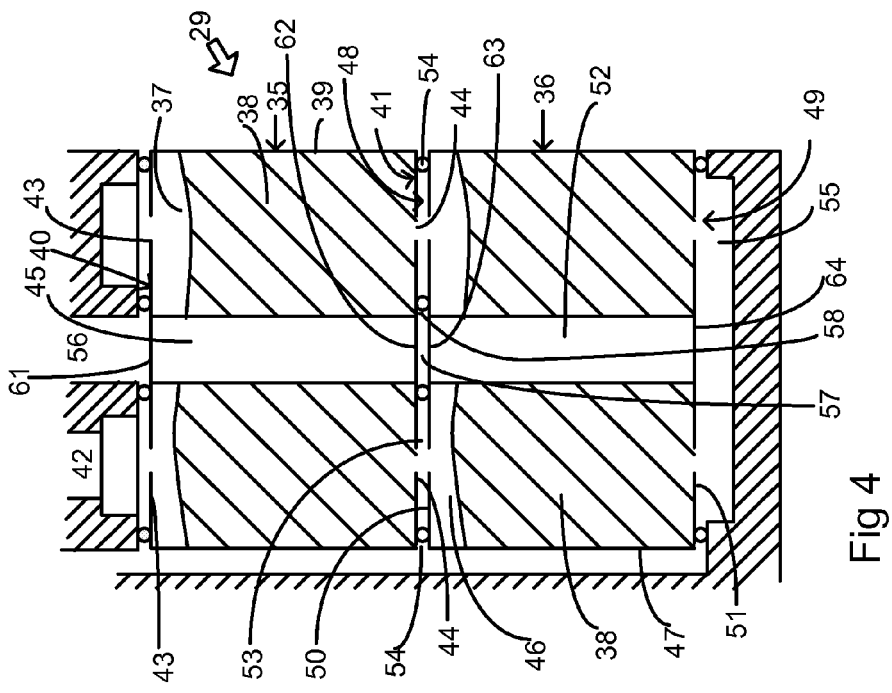
FIG. 4 is a schematic view of a housing assembly for a solid fluidal substance removing an undesired respiratory gas component of a respiratory gas flow in accordance with an embodiment.
Figure 2:
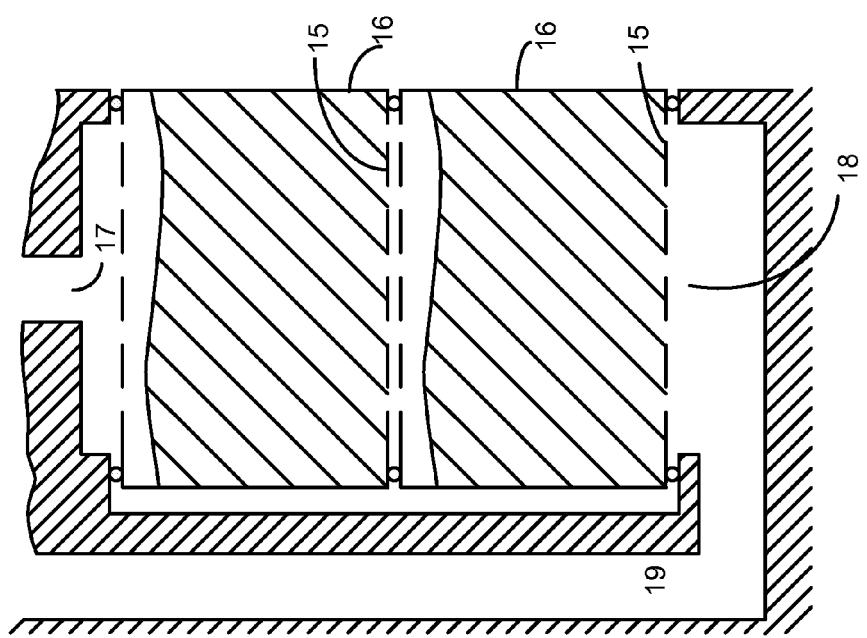
FIG. 2 is a schematic view of prior art cartridges connected to a breathing system.

FIG. 4 presents a schematic drawing of the housing assembly 29 comprising first housing 35 and a second housing 36 such as absorber canisters. The first housing 35 and the second housing 36 are in series allowing the respiratory gas flow first through the first housing and then after the second housing. Typically they may be one on the other. Within the first housing 35 there is a first space 37 receiving the substance 38, which may be solid and fluidal material, used in this embodiment to absorb carbon dioxide of the respiratory gas. The first housing comprises a first wall 39 surrounding a part of the first space 39. The first housing also comprising a first end 40 and a second end 41 operationally connected to the first wall 39 and which first end surrounds part of the first space 37 and which second end surrounds part of the first space 37. The first end comprises a first opening 43 for the gas communication with the first space 37 and the second end 41 comprises a second opening 44 for the communication with the first space 37. From a first gas port 42 which is in flow communication with the expiration limb 28 of the breathing circuit 26 the respiratory gas is guided to the first opening 43 of the first housing and through the first space 37 filled with the substance 38 to the second opening 44.

This first opening 43 and the second opening 44 may also comprise a separator (not shown in Figure) allowing gas flow through but preventing the substance escaping through it. Alternatively the separator may be functionally integrated with the first end and second end. Further the first housing comprises a first channel 45 between the first end and the second end returning in this specific embodiment the gas flowed through the first space to the first end which happens after the gas has passed through the second housing 36, too. At the first end 40 there is a first orifice 61 in gas flow communication with the first channel 45 and at the second end 41 there is a second orifice 62 in gas flow communication with the first channel 45, too. The first channel may be an integral part of the first housing, advantageously within the first wall 39 or centrically in said housing and surrounded by the first space 37 and an edge of this channel is substantially gas tight to avoid mixing of the respiratory gas flowing within the first space and the gas flowing along the first channel.

The first housing is a separate component and may be detachable from the housing assembly and when detached the first orifice and the first opening at the first end and correspondingly the second orifice and the second opening at the second end of the first housing are opening outside the first housing, which may also mean that they are opening to surrounding environment for instance to the second housing. Thus the first housing may fail to connect the first orifice and the first opening at the first end and correspondingly fails to connect the second orifice and the second opening at the second end.

Within the second housing 36, that is advantageously equal to the first housing 35, there is a second space 46 receiving the substance 38, which may be solid and fluidal material, used in this embodiment to absorb carbon dioxide of the respiratory gas and a second wall 47 surrounding a part of the second space 46. The second housing also comprising a third end 48 and a fourth end 49 operationally connected to the second wall 47 and which third end surrounds part of the second space 46 and which second end surrounds part of the second space 46. The third end comprises a third opening 50 for the gas communication with the second space 46 and the fourth end 49 comprises a fourth opening 51 for the gas communication with the second space 46. From the second opening 44 the respiratory gas flows to the third opening 50 and through it and through the second space 46 filled with the substance 38 to the fourth opening 51. This third opening 50 and the fourth opening 51 may also comprise a separator (not shown in Figure) allowing gas flow through but preventing the substance escaping through it. Alternatively the separator may be functionally integrated with the first end and second end. Further the second housing comprises a second channel 52 between the third end 48 and the fourth end 49 returning in this specific embodiment the gas flowed through the second space to the third end. At the third end 48 there is a third orifice 63 in gas communication with the second channel 52 and at the fourth end 49 there is a fourth orifice 64 in gas communication with the second channel 52, too. The second channel 52 may be an integral part of the second housing, advantageously within the second wall 47 or centrically in said housing and surrounded by the second space 46 and an edge of this channel is substantially gas tight to avoid mixing of the respiratory gas flowing within the second space 46 and the gas flowing along the second channel 52.

The second opening of said first housing is in flow communication, advantageously in direct flow communication, with outside the first housing such as the third opening of the second housing to guide the gas flow between the first space and the second space. The second orifice of the first housing is in flow communication, advantageously in direct flow communication, with outside the first housing such as the third orifice of the second housing to guide the gas flow between the first orifice and the fourth orifice. Thus the respiratory gas flows or is guided further from the second opening 44 of the first housing to the third opening 50 at the third end 48 of the second housing 36 and through the second space 46 filled with the substance 38 to the fourth opening 51. Between the second opening 44 of the first housing and the third opening 50 of the second housing there may be a first intermediate chamber 53 surrounded by a first washer 54 as shown in FIG. 4 to prevent gas escaping from this chamber or to prevent surrounding gas mixing with the respiratory gas. The second opening 44 and the third opening 50 can also be connected together without the intermediate chamber.

From the fourth opening 51 of the second housing 36 the respiratory gas is guided to the flow-turn chamber 55, which is preferably outside the second housing. The flow-turn chamber connects the respiratory flow path of the second space 46 of the second housing 36 to the fourth orifice and the second channel 52 which may be within the second housing as shown in FIG. 4. This second channel is in gas communication with the first channel 45 of the first housing 35 forming a gas flow path between the flow-turn chamber 55 or the fourth end 49 and the first end 40 or a second gas port 56 which is in flow communication with the inspiration limb 27 of the breathing circuit 26. Between the first channel 45 of the first housing 35 and the second channel 52 of the second housing 36 there may be a second intermediate chamber 57 surrounded by a second washer 58 as shown in FIG. 4. The first channel 45 and the second channel 52 can also be connected together without the second intermediate chamber.

Depending on the application the gas may flow on either direction through the first housing 35 and the second housing 36. The gas flow between the first space and the second space is into different direction than the gas flow between the first channel and the second channel. Typically these flow directions are opposite. Thus the first gas port 42 can work besides an inlet port also as an outlet port and likewise the second gas port 56 can work besides as an outlet port also as an inlet port, so their roles may change.

The first housing 35 and the second housing 36 in FIG. 4 represents the return flow path at the middle and the flow path through the substance 38 at the side. However, any other configuration is possible as well. The first and second channels e.g. may be arranged cylindrically at the wall or as an integral separate channel that follows the wall. The first channel may be an integral part of the first housing and the second channel may be an integral part of the second housing. Both the first channel 45 and the gas flow path through the substance of the first space 37 form a pathway between the first end 40 and the second end 41. Correspondingly both the second channel 52 and the gas flow path through the substance of the second space 46 form a pathway between the third end 48 and the fourth end 49. The first housing has the first opening 43 and the second opening 44 for the flow path through the substance 38 and the first channel 45 which may be also vertical. Similarly the second housing has the third opening 50 and the fourth opening 51 for the flow path through the substance 38 and the second channel 52.

Figure 5:
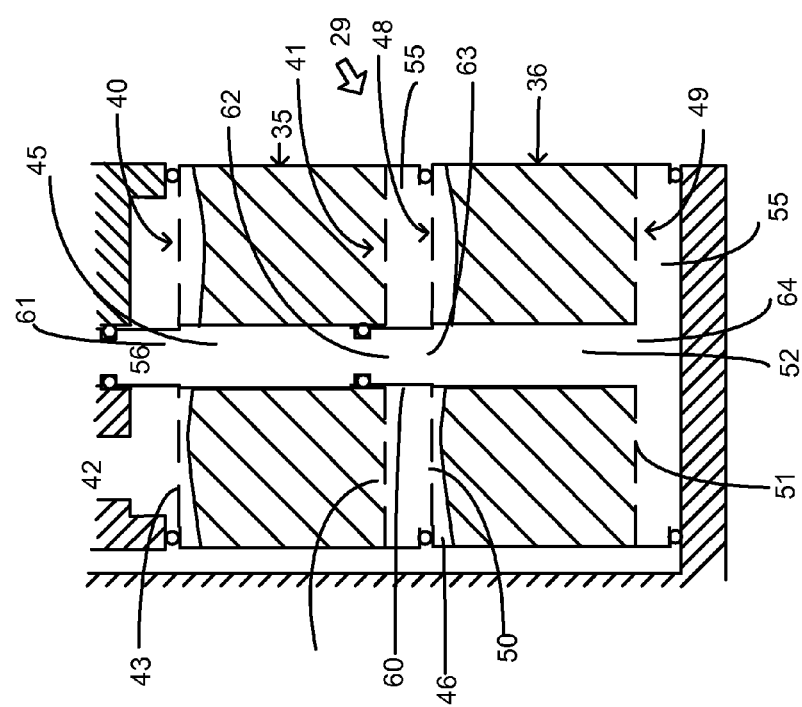
FIG. 5 is a schematic view of a housing for a solid fluidal substance removing an undesired respiratory gas component of a respiratory gas flow in accordance with another embodiment.

Another embodiment of the housing assembly 29 is presented in FIG. 5. There the flow-turn chamber 55 is in the second housing 36 instead of being separate on the receptacle mechanics of the breathing system as is the case in FIG. 4. The flow turn chamber may at least partly connect the respiratory flow path from the fourth opening 51 to the second channel 52. The flow-turn chamber can be integrated with the second housing. This can be done by having gas connections on one side of the housing and having on another side of the housing sealable openings. On new housing when taken into use on the second position 36 these openings would be closed but get opened to allow gas flow through when moved for the first housing. These openings may be punctuable when interfaced by gas connectors or sealed by sealing surface the second absorber is interfacing. To make the first housing 35 similar with the second housing 36 also the first housing is provided with similar flow-turn chamber 55, but this flow-turn chamber is occluded by a first extension tube 60, which may be integrated into the second housing 36 or its second channel 52, to prevent the gas flow directly from the second opening 44 to the first channel 45 of the first housing when the second housing is connected to it, but guiding the respiratory gas flow from the second opening 44 to the third opening 50 and through the second space 46 and the fourth opening 51 to the flow-turn chamber 55 of the second housing 36. The flow-turn chamber of the second housing 36 is left open allowing the gas flow between the fourth opening 51 and the second channel 52.

In both embodiments shown in FIGS. 4 and 5 depending on the flow direction the substance 38 either in the first housing 35 or in the second housing 36 is first consumed and the housing including the substance 38 which was first consumed is removed and replaced with the remaining housing including still active or usable substance. In case the first housing 35 is receiving the respiratory gas flow first and thus its substance consumed first and the transfer zone has penetrated through the first space 37, the second housing 36 is moved to first latest when the CO2 penetrates through the latter. To make the first housing and second housing changeable, they should be similar, advantageously identical. When one of the housings is removed, then a new housing with the substance 38 is assembled into the housing assembly 29 to maintain the number of housings unchanged in the housing assembly.

Embodiments explained hereinbefore allows dual housing without the cleaning burden and are based on inclusion of the return flow path integrated into the first and second housing to provide single gas interface surface towards the breathing circuit 26. An advantage of using dual housing is the effective use of the absorbent material reducing formation of alcalic chemical waste and the packaging waste of the housing by reducing the number of housings consumed.

It is not necessary to have both the first housing and the second housing, but only one housing introduced hereinbefore can be used in case the housing assembly is designed for one single housing.

The written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

We claim:

1. A housing for a substance removing an undesired respiratory gas component of a respiratory gas flow comprising:
    a first space for receiving said substance;
    a first wall surrounding part of said first space and extending beyond the first space to define a first flow redirection chamber, the first flow redirection chamber configured to redirect the respiratory gas flow;
    a first end operationally connected to said first wall and surrounding part of said first space, said first end comprising a first opening for the gas communication with said first space;
    a second end operationally connected to said first wall and surrounding part of said first space, said second end comprising a second opening for the gas communication with said first space; and
    a first channel between said first end and said second end for guiding the gas flow, said first channel comprising a first orifice at said first end and a second orifice at said second end, said first orifice and said second orifice being in gas communication with said first channel, said first channel extending beyond said first space at said first end to define a first extension tube, said second end defining a cavity for receiving a second extension tube,
    wherein said first orifice and said first opening at said first end are adapted to be in flow communication with outside said housing, and
    wherein said second orifice and said second opening at said second end of said housing are adapted to be in flow communication with said first flow redirection chamber.

2. The housing according to claim 1, wherein said first orifice and said first opening at said first end and that said second orifice and said second opening at said second end of said housing are adapted to open outside said housing to surrounding environment.

3. The housing according to claim 1, wherein said housing is adapted to fail to connect said first orifice and said first opening at said first end and that said housing is adapted to fail to connect said second orifice and said second opening at said second end of said housing and that said second end is opposite said first end.

4. The housing according to claim 1, wherein said first opening is adapted to guide gas flow to said first space and said second opening is adapted to guide gas flow from said first space outside said housing in which case said second orifice is adapted to guide gas flow guided through said first space to said first channel and said first orifice is adapted to guide gas flow from said first channel outside said housing.

5. The housing according to claim 1, wherein said first orifice is adapted to guide gas flow to said first channel and said second orifice is adapted to guide gas flow from said first channel outside said housing in which case said second opening is adapted to guide gas flow to said first space and said first opening is adapted to guide gas flow from said first space outside said housing.

6. The housing according to claim 1, wherein said first channel is an integral part of said housing.

7. The housing according to claim 1, wherein said first channel is within said first wall, advantageously centrically in said housing.

8. The housing according to claim 1, wherein said first space is adapted to surround said first channel between said first end and said second end.

9. The housing according to claim 1, wherein said substance is a chemical compound removing carbon dioxide.

10. A housing assembly for a substance removing an undesired respiratory gas component of a respiratory gas flow comprising:
    a first housing having a first space for receiving said substance; a first wall surrounding part of said first space and extending beyond the first space to define a first flow redirection chamber, the first flow redirection chamber configured to redirect the respiratory gas flow; a first end operationally connected to said first wall and surrounding part of said first space, said first end comprising a first opening for the gas communication with said first space; a second end operationally connected to said first wall and surrounding part of said first space, said second end comprising a second opening for the gas communication with said first space; and a first channel between said first end and said second end for guiding the gas flow, said first channel comprising a first orifice at said first end and a second orifice at said second end, said first orifice and said second orifice being in flow communication with said first channel, and
    a second housing having a second space for receiving said substance; a second wall surrounding part of said second space; a third end operationally connected to said second wall and surrounding part of said second space, said third end comprising a third opening for the gas communication with said second space; a fourth end operationally connected to said second wall and surrounding part of said second space, said fourth end comprising a fourth opening for the gas communication with said second space; and a second channel between said third end and said fourth end for guiding the gas flow, said second channel extending beyond said second space to define a first extension tube, said second channel comprising a third orifice at said third end and a fourth orifice at said fourth end, said third orifice and said fourth orifice being in flow communication with said second channel, said first extension tube extending through said first flow redirection chamber to connect to said first channel;
    wherein said second opening of said first housing is adapted to be in flow communication with said third opening of said second housing to guide the gas flow between said first space and said second space and said second orifice of said first housing is adapted to be in flow communication with said third orifice of said second housing to guide the gas flow between said first orifice and said fourth orifice.

11. The housing assembly according to claim 10, wherein both of said first channel and said second channel is adapted to guide the gas flow through said first housing and said second housing passing said first space and said second space.

12. The housing assembly according to claim 10, wherein said first housing and said second housing are adapted to be in series and that said second end of said first housing is opposite said first end of said first housing and that said fourth end of said second housing is opposite said third end of said second housing.

13. The housing assembly according to claim 10, wherein said first housing and said second housing are adapted to be one on the other.

14. The housing assembly according to claim 10, wherein said first housing and said second housing are similar or even identical and that said second end is opposite said first end and that said fourth end is opposite said third end.

15. The housing assembly according to claim 10, wherein said first housing and said second housing are changeable enabling one of them having the substance consumed by the undesired gas component to be replaced by the remaining one with still usable substance.

16. The housing assembly according to claim 15, wherein a new housing similar to the first and second housing is assembled into the housing assembly to maintain the number of housings unchanged.

17. The housing assembly according to claim 10 further comprising a flow-turn chamber at least partly connecting the respiratory flow path from said fourth opening to said second channel.

18. The housing assembly according to claim 10, wherein the gas flow between said first space and said second space is adapted to be into different direction than the gas flow between said first channel and said second channel.

19. An arrangement for ventilating lungs of a subject comprising:
 a ventilator for supplying a breathing gas for an inspiration and for receiving a breathing gas for an expiration;
 a gas mixer for supplying a fresh gas for the subject breathing; and
 a breathing circuit for connecting lungs of the subject, said ventilator and said gas mixer, said breathing circuit comprising an inspiration limb providing an inspiration gas including the fresh gas for the subject breathing; an expiration limb to discharge an expiration gas; and a housing assembly for a substance removing an undesired respiratory gas component of a respiratory gas flow, said housing assembly comprising:
 a first housing having a first space for receiving said substance; a first wall surrounding part of said first space and extending beyond the first space to define a first flow redirection chamber, the first flow redirection chamber configured to redirect the respiratory gas flow; a first end operationally connected to said first wall and surrounding part of said first space, said first end comprising a first opening for the gas communication with said first space; a second end opposite said first end operationally connected to said first wall and surrounding part of said first space, said second end comprising a second opening for the gas communication with said first space; and a first channel between said first end and said second end for guiding the gas flow, said first channel comprising a first orifice at said first end and a second orifice at said second end, said first orifice and said second orifice being in flow communication with said first channel, and
 a second housing having a second space for receiving said substance; a second wall surrounding part of said second space; a third end operationally connected to said second wall and surrounding part of said second space, said third end comprising a third opening for the gas communication with said second space; a fourth end opposite said third end operationally connected to said second wall and surrounding part of said second space, said fourth end comprising a fourth opening for the gas communication with said second space; and a second channel between said third end and said fourth end for guiding the gas flow, said second channel extending beyond said second space to define a first extension tube, said second channel comprising a third orifice at said third end and a fourth orifice at said fourth end, said third orifice and said fourth orifice being in flow communication with said second channel, said first extension tube extending through said first flow redirection chamber to connect to said first channel;
 wherein said second opening of said first housing is adapted to be in flow communication with said third opening of said second housing to guide the gas flow between said first space and said second space and said second orifice of said first housing is adapted to be in flow communication with said third orifice of said second housing to guide the gas flow between said first orifice and said fourth orifice.

20. The arrangement according to claim 19, wherein the gas flow between said first space and said second space is adapted to be into different direction than the gas flow between said first channel and said second channel.

* * * * *